United States Patent [19]

Das et al.

[11] Patent Number: 4,466,979
[45] Date of Patent: Aug. 21, 1984

[54] 7-OXABICYCLOHEPTANE SUBSTITUTED CARBAMATE PROSTAGLANDIN ANALOGS USEFUL IN TREATING PLATELET AGGREGATION AND BRONCHOCONSTRICTION

[75] Inventors: Jagabandhu Das, Plainsboro; Martin F. Haslanger, Lambertville, both of N.J.

[73] Assignee: E. R. Squibb & Sons, Inc., Princeton, N.J.

[21] Appl. No.: 459,847

[22] Filed: Jan. 21, 1983

[51] Int. Cl.$^3$ .................. A61K 31/34; A61K 31/557; C07D 307/00
[52] U.S. Cl. .................. 424/285; 549/463
[58] Field of Search .................. 549/463; 424/285

[56] References Cited

U.S. PATENT DOCUMENTS

| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 32292 6/1982 European Pat. Off. .
2039909 8/1980 United Kingdom .

Primary Examiner—Henry R. Jiles
Assistant Examiner—Bernard Dentz
Attorney, Agent, or Firm—Lawrence S. Levinson; Burton Rodney

[57] ABSTRACT

7-Oxabicycloheptane substituted carbamate prostaglandin analogs are provided having the structural formula

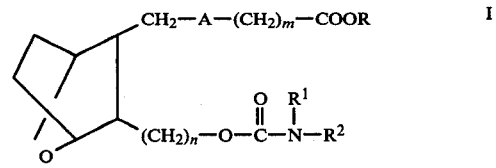

and including all stereoisomers thereof.

The compounds are cardiovascular agents useful, for example, in the treatment of thrombolytic disease.

12 Claims, No Drawings

7-OXABICYCLOHEPTANE SUBSTITUTED CARBAMATE PROSTAGLANDIN ANALOGS USEFUL IN TREATING PLATELET AGGREGATION AND BRONCHOCONSTRICTION

DESCRIPTION OF THE INVENTION

The present invention relates to 7-oxabicycloheptane substituted carbamate prostaglandin analogs which are cardiovascular agents useful, for example, in the treatment of thrombolytic disease. These compounds have the structural formula

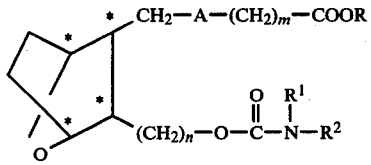

and including all stereoisomers thereof, wherein

A is CH=CH or $(CH_2)_2$; m is 1 to 8; n is 1 to 5, R is H or lower alkyl; and $R^1$ and $R^2$ may be the same or different and are hydrogen, lower alkyl, aryl, aralkyl, lower alkoxy, aralkoxy or cycloalkyl, with the proviso that at least one of $R^1$ and $R^2$ is other than hydrogen.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The terms "$(CH_2)_m$" and "$(CH_2)_n$" includes a straight or branched chain radical having from 1 to 8 carbons in the normal chain in the case of "$(CH_2)_m$" and 1 to 5 carbons in the normal chain in the case of "$(CH_2)_n$" and may contain one or more lower alkyl substituents. Examples of $(CH_2)_m$ and $(CH_2)_n$ groups include $CH_2$, $CH_2CH_2$, $(CH_2)_3$, $(CH_2)_4$, $(CH_2)_5$, $(CH_2)_6$, $(CH_2)_7$,

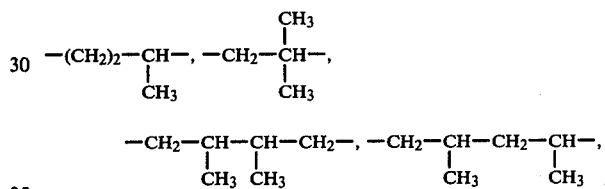

and the like.

Preferred are those compounds of formula I wherein A is $(CH_2)_2$ or CH=CH, m is 2 to 4, R is H, n is 1, and $R^1$ is hydrogen and $R^2$ is lower alkyl, aryl, such as phenyl, or benzyl.

The various compounds of the invention may be prepared as outlined below.

A. Where n is 1 and A is CH=CH

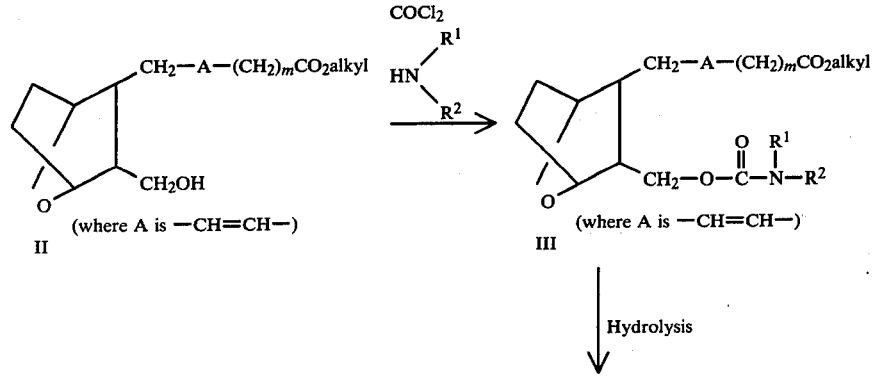

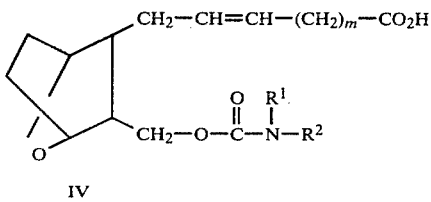
IV
B. Where n is 1 and A is $(CH_2)_2$
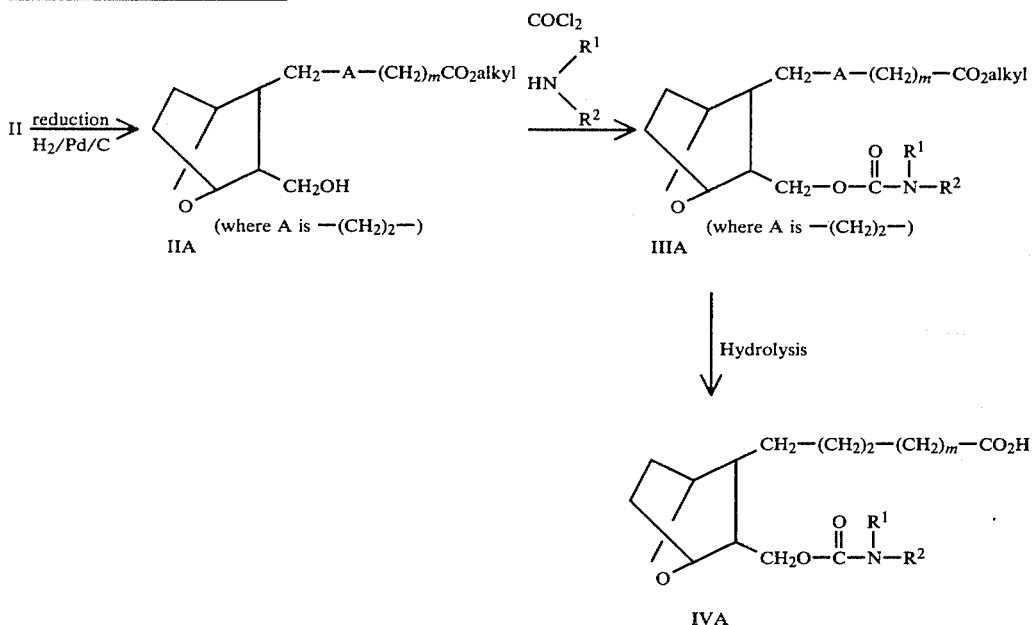
C. Where n is 2 to 5
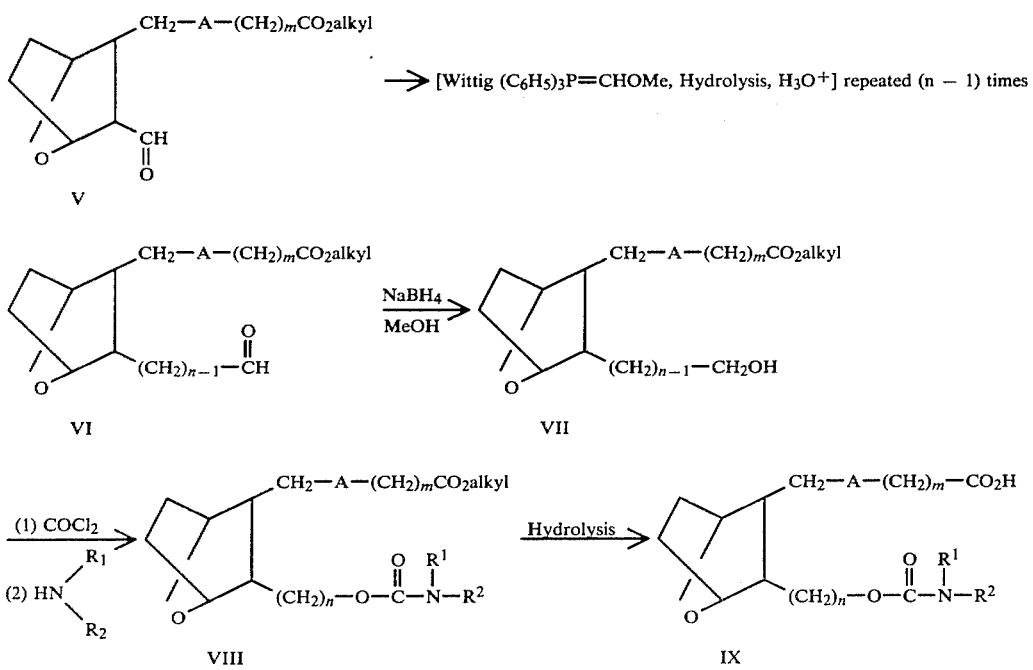
As seen in the reaction sequence identified as "A" and "B", compounds of the invention wherein n is 1,

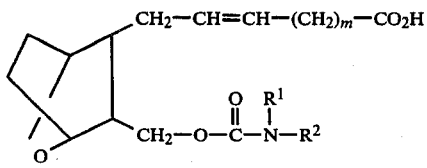

IV

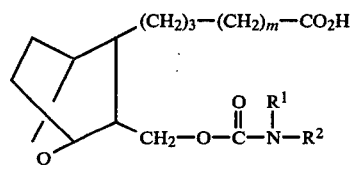

IVA may be prepared by reacting the starting lower alkyl ester II (A is CH=CH) or IIA (A is (CH$_2$)$_2$) (prepared as described in U.S. Pat. No. 4,143,054) with a secondary amine of the structure

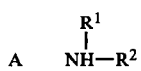

in the presence of phosgene and preferably in an inert atmosphere employing a molar ratio of II or IIA:A of within the range of from about 0.5:1 to about 1:1. The resulting alkyl ester III or IIIA is then subjected to hydrolysis to form the acid IV or IVA by treating the esters with a base such as lithium hydroxide, followed by neutralization with an acid such as dilute hydrochloric acid or oxalic acid.

In the reaction sequence identified as "C", the aldehyde III or IIIA is used to prepare aldehyde VI (where n is 2–5) by carrying out a homologation sequence, such as a Wittig reaction with (C$_6$H$_5$)$_3$P=CHOMe followed by hydrolysis, (n−1) times. The aldehyde VI (where n=2−5) is thus carried on to the compounds of this invention where n is 2−5, that is

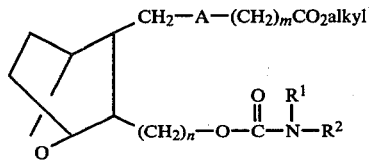

IVB by reduction employing a reducing agent such as sodium borohydride in a solvent such as methanol to form the alcohol VII

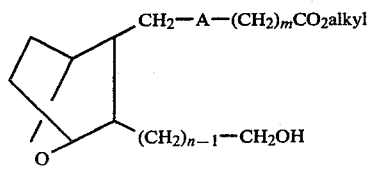

VII which is reacted with an amine

in the presence of phosgene to form the compound of the invention VIII

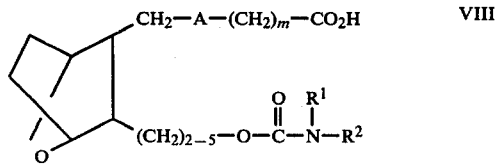

VIII

Compound VIII may then be hydrolyzed to the corresponding acid IX.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis exo, cis endo and all trans forms and stereoisomeric pairs may be prepared as shown in the working Examples which follow and by employing starting materials and following the procedures as outlined in U.S. Pat. No. 4,143,054. Examples of such stereoisomers are set out below.

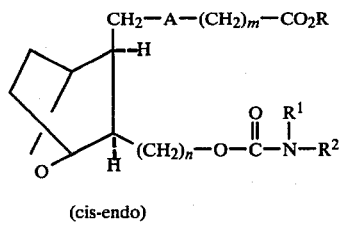

(cis-endo)

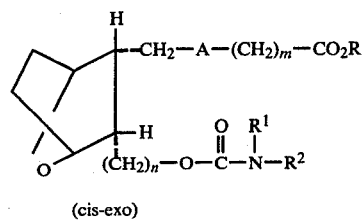

(cis-exo)

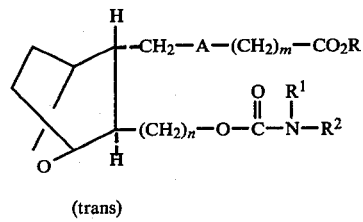

(trans)

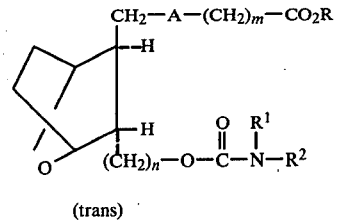

(trans)

The nucleus in each of the compounds of the invention is depicted as

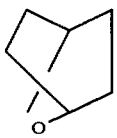

for matter of convenience; it will also be appreciated that the nucleus in the compounds of the invention may be depicted as

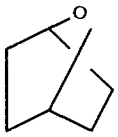

The compounds of this invention inhibit arachidonic acid-induced platelet aggregation and bronchoconstriction. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of this invention may also be administered topically to treat peripheral vascular diseases and as such may be formulated as a cream or ointment.

The following Examples represent preferred embodiments of the invention.

EXAMPLE 1

[1β,2α(5Z),3α,4β]-7-[3-[[[(Butylamino)carbonyl]oxy]-methyl]-7-oxabicyclo[2.2.1]hept-2-yl]-5-heptenoic acid, methyl ester To a solution of 402 mg of [1β,2α(5Z),3α,4β]-7-[3-(hydroxymethyl)-7-oxabicyclo[2.2.1]hept-2-yl]-5-heptenoic acid, methyl ester (prepared as described in U.S. Pat. No. 4,143,054) (1.5 mmole) in 5 ml of methylene chloride was added dropwise at room temperature, 5 ml of a 12.5% by weight solution of phosgene in benzene (3.6 mmole). After stirring for 1 hour at room temperature, argon was bubbled through the reaction mixture to remove excess of phosgene. It was then cooled in an ice-water bath and 500 μl of freshly distilled n-butylamine (5 mmole) was added dropwise. The reaction mixture was warmed to room temperature and stirred for additional 1 hour, whereupon it was diluted with ether and filtered through anhydrous magnesium sulfate. The filtrate was concentrated in vacuo and chromatographed on a silica gel column (flash chromatography, LPS-1 silica gel) and eluted with 50% ethylacetate in hexane to give 440 mg of the title carbamate (80% yield).

EXAMPLE 2

[1β,2α(5Z),3α,4β]-7-[3-[[[(Butylamino)carbonyl]oxy]-methyl]-7-oxabicyclo[2.2.1]hept-2-yl]-5-heptenoic acid To a solution of 400 mg of the Example 1 carbamate in 6 ml of distilled THF was added with stirring 2 ml of 1N aqueous lithium hydroxide solution and 0.5 ml of water. The reaction mixture was stirred at room temperature for 6 hours, whereupon it was diluted with methylene chloride and washed thoroughly with saturated salt solution. The organic layer was dried over anhydrous magnesium sulfate and concentrated in vacuo to give 330 mg of the title acid (90% crude yield). Further purification by chromatography on a silica gel column (CC-7 silica gel) and elution with 50% ethylacetate in methylene chloride gave analytically pure title acid.

TLC-$R_f$ 0.39 (50% $CH_2Cl_2$ in EtOAc) $R_f$ 0.67 (EtOAc) Anal Calcd for $C_{19}H_{31}NO_5$: C, 64.56; H, 8.84; N, 3.96 Found: C, 64.56; H, 8.65; N, 3.70

EXAMPLE 3

[1β,2α(5Z),3β,4β]-7-[3-[[[[(Butyl)methylamino]-carbonyl]oxy]methyl]-7-oxabicyclo[2.2.1]hept-2-yl]-5-heptenoic acid, methyl ester To a solution of 402 mg of [1β,2α(5Z),3β,4β]-7-[3-(hydroxymethyl)-7-oxabicyclo[2.2.1]hept-2-yl]-5-heptenoic acid, methyl ester (prepared as described in U.S. Pat. No. 4,143,054) (1.5 mmole) in 5 ml of methylene chloride is added dropwise at room temperature, 5 ml of a 12.5% by weight solution of phosgene in benzene (3.6 mmole). After stirring for 1 hour at room temperature, argon is bubbled through the reaction mixture to remove excess of phosgene. It is then cooled in an ice-water bath and 500 μl of freshly distilled (n-butyl)methylamine (5 mmole) is added dropwise. The reaction mixture is warmed to room temperature and stirred for additional 1 hour, whereupon it is diluted with ether and filtered through anhydrous magnesium sulfate. The filtrate is concentrated in vacuo and chromatographed on a silica gel column (flash chromatography, LPS-1 silica gel) and eluted with 50% ethylacetate in hexane to give the title carbamate.

EXAMPLE 4

[1β,2α(5Z),3β,4β]-7-[3-[[[[(Butyl)methylamino]-carbonyl]oxy]methyl]-7-oxabicyclo[2.2.1]hept-2-yl]-5-heptenoic acid To a solution of 400 mg of the Example 1 carbamate in 6 ml of distilled THF is added with stirring 2 ml of 1N aqueous lithium hydroxide solution and 0.5 ml of water. The reaction mixture is stirred at room temperature for 6 hours, whereupon it is diluted with methylene chloride and washed thoroughly with saturated salt solution. The organic layer is dried over anhydrous magnesium sulfate and concentrated in vacuo to give 330 mg of title acid (90% crude yield). Further purification by chromatography on a silica gel column (CC-7 silica gel) and elution with 50% ethyl-acetate in methylene chloride gives analytically pure title acid.

EXAMPLE 5

(1β,2β,3α,4β)-7-[3-[[[(Phenylamino)carbonyl]oxy]-methyl]-7-oxabicyclo[2.2.1]hept-2-yl]heptanoic acid A. (1β,2β,3β,4β)-7-[3-(Hydroxymethyl)-7-oxabicyclo[2.2.1]hept-2-yl]heptanoic acid, methyl ester To 800 mg (3.0 mmole) of the [1β,2β(5Z),-3β,4β]-7-[3-(hydroxymethyl)-7-oxabicyclo[2.2.1]hept-2-yl]-5-heptenoic acid, methyl ester as prepared in U.S. Pat. No. 4,143,054, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B. (1β,2β,3β,4β)-7-[3-Formyl-7-oxabicyclo[2.2.1]hept-2-yl]heptanoic acid, methyl ester To 1.21 g (5.6 mmole, 2.0 equiv.) of pyridinium chlorochromate (PCC) and 20 ml of anydrous $CH_2Cl_2$ was added, under an argon atmosphere, 730 mg (2.8 mmole) of the title A alcohol in 2 ml of $CH_2Cl_2$. The reaction was stirred for 2 hours at 25°, diluted with 100 ml of ether, filtered through a pad of florisil, and evaporated to furnish 670 mg (88%) of the title B compound as a white crystalline solid.

C. (1β,2β,3α,4β)-7-[3-Formyl-7-oxabicyclo[2.2.1]hept-2-yl]heptanoic acid, methyl ester To 800.0 mg of the title B aldehyde in 20 ml of anhydrous methanol under an argon atmosphere at 25° was added 100 mg of sodium methoxide. The reaction was stirred for 2 hours, diluted with 100 ml of saturated ammonium chloride and extracted with four 100 ml portions of ether. The ethereal layer was washed with 50 ml of brine dried over anhydrous magnesium sulfate and concentrated to afford 765.0 mg (98%) of the title C aldehyde.

D. (1β,2β,3α,4β)-7-[3-[[[(Phenylamino)-carbonyl]oxy]methyl]-7-oxabicyclo[2.2.1]hept-2-yl]heptanoic acid Following the procedure of Example 1, except substituting the Part C aldehyde for the Example 1A aldehyde and substituting aniline for butylamine, the title product is obtained.

EXAMPLE 6

[1β,2α(5Z),3α,4β]-7-[[[(Cyclohexylamino)carbonyl]oxy]methyl]-7-oxabicyclo[2.2.1]hept-2-yl]-5-heptenoic acid Following the procedure of Examples 1 and 2 except substituting cyclohexylamine for butylamine the title compound is obtained.

EXAMPLE 7

[1β,2α(5Z),3β,4β]-7-[3-[[[(Ethoxyamino)carbonyl]oxy]methyl]-7-oxabicyclo[2.2.1]hept-2-yl]-5-heptenoic acid Following the procedure of Examples 3 and 4 except substituting ethoxyamine for butylamine, the title compound is obtained.

EXAMPLE 8

(1β,2β,3α,4β)-7-[3-[[[(Benzylamino)carbonyl]oxy]methyl]-7-oxabicyclo[2.2.1]hept-2-yl]heptanoic acid Following the procedure of Example 5 except substituting benzylamine for butylamine, the title compound is obtained.

EXAMPLE 9

[1β,2α(5Z),3α,4β]-7-[3-[[[(Benzyloxyamino)carbonyl]oxy]methyl]-7-oxabicyclo[2.2.1]hept-2-yl]-5-heptenoic acid Following the procedure of Examples 1 and 2 except substituting benzyloxyamine for butylamine, the title compound is obtained.

EXAMPLE 10

[1β,2α(5Z),3β,4β]-7-[3-[[[[(Ethyl)phenylamino]-carbonyl]oxy]methyl]-7-oxabicyclo[2.2.1]hept-2-yl]-5-heptenoic acid Following the procedure of Examples 3 and 4 except substituting (ethyl)phenylamine for butylamine, the title compound is obtained.

EXAMPLE 11

(1β,2β,3α,4β)-7-[3-[[[[(Cyclopentyl)methylamino]-carbonyl]oxy]methyl]-7-oxabicyclo[2.2.1]hept-2-yl]-heptanoic acid Following the procedure of Example 5 except substituting (cyclopentyl)methylamine for butylamine, the title compound is obtained.

EXAMPLE 12

[1β,2α(5Z),3α,4β]-7-[3-[[[[(Phenylethyl)amino]-carbonyl]oxy]methyl]-7-oxabicyclo[2.2.1]hept-2-yl]-5-heptenoic acid Following the procedure of Examples 1 and 2 except substituting (phenylethyl)amine for butylamine, the title product is obtained.

EXAMPLE 13

[1β,2α(5Z),3α,4β]-7-[3-[[[(Butylamino)carbonyl]oxy]ethyl]-7-oxabicyclo[2.2.1]hept-2-yl]-5-heptenoic acid A. [1β,2α(5Z),3α,4β]-7-[3-(2-Oxo)ethyl-7-oxabicyclo[2.2.1]hept-2-yl]-5-heptenoic acid, methyl ester Into a dry 1000 ml round bottom 3-necked flask containing a stir bar was added dried 12.9 g (37.7 mmoles) methoxymethyltriphenylphosphonium chloride (($C_6H_5$)$_3$P+—$CH_2OCH_3Cl$−) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1β,2α(5Z),3α,4β]-7-[3-formyl-7-oxabicyclo[2.2.1]-hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated $NH_4Cl$, and extracted with ether (4×200 ml). The combined ether phases were washed with NaCl, saturated solution, and dried (MgSO$_4$) and concentrated to yield a yellow oil in a white crystalline solid (phosphine oxide). The white solid was triturated with EtOAc and purified by chromatography on an LPS-1 silica column. The fractions obtained were (A) [1β,2α(5Z),3α,4β]-7-[3-(2-oxo)ethyl-7-oxabicyclo[2.2.1]hept-2-yl]-5-heptenoic acid, methyl ester, (B) [1β,2α(5Z),3α,4β]-7-[3-(2-methoxy)ethendiyl- 7-oxabicyclo[2.2.1]hept-2-yl]-5-heptenoic acid, methyl ester, and (C) [1β,2α(5Z),3α,4β]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (C).

B. [1β,2α(5Z),3α,4β]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with NaBH₄ (0.19 g, 5 mmol) in an argon atmosphere at 0° C. After stirring at 0° for 1 hour, the reaction is quenched by addition 2N HCl (to pH 2). The methanol is removed in vacuo and the reaction mixture is taken up in ether. The ether solution is washed with saturated KHCO₃, saturated NaCl and dried (MgSO₄). The ether is evaporated to yield the title B compound.

C. [1β,2α(5Z),3α,4β]-7-[3-[[[(Butylamino)-carbonyl]oxy]ethyl]-7-oxabicyclo[2.2.1]-hept-2-yl]-5-heptenoic acid Following the procedure of Example 1 except substituting the above part B alcohol for the alcohol used in Example 1, the title compound is obtained.

EXAMPLE 14

[1β,2α(5Z),3β,4β]-7-[3-[[[(Butylamino)carbonyl]-oxy]ethyl]-7-oxabicyclo[2.2.1]hept-2-yl]-5-heptenoic acid Following the procedure of Example 13, except substituting [1β,2α(5Z),3β,4β]-7-[3-formyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title compound is obtained.

EXAMPLE 15.

(1β,2β,3α,4β)-7-[3-[[[(Butylamino)carbonyl]oxy]-ethyl]-7-oxabicyclo[2.2.1]hept-2-yl]heptanoic acid Following the procedure of Example 13 except substituting (1β,2β,3α,4β)-7-[3-formyl-7-oxabicyclo[2.2.1-]hept-2-yl]heptanoic acid, methyl ester for [1β,2α(5Z),3β,4β]-7-[3-formyl-7-oxabicyclo[2.2.1]hept-2-yl]-5-heptenoic acid, methyl ester, the title compound is obtained.

EXAMPLE 16

[1β,2α(5Z),3α,4β]-7-[3-[[[(Cyclohexylamino)carbonyl]-oxy]ethyl]-7-oxabicyclo[2.2.1]hept-2-yl]-5-heptenoic acid Following the procedure of Example 13 except substituting cyclohexylamine for butylamine the title compound is obtained.

EXAMPLE 17

[1β,2α(5Z),3β,4β]-7-[3-[[[(Ethoxyamino)carbonyl]-oxy]ethyl]-7-oxabicyclo[2.2.1]hept-2-yl]-5-heptenoic acid Following the procedure of Example 14 except substituting ethoxyamine for butylamine, the title compound is obtained.

EXAMPLE 18

(1β,2β,3α,4β)-7-[3-[[[(Benzylamino)carbonyl]oxy]-ethyl]-7-oxabicyclo[2.2.1]hept-2-yl]heptanoic acid Following the procedure of Example 15 except substituting benzylamine for butylamine, the title compound is obtained.

EXAMPLE 19

[1β,2α(5Z),3α,4β]-7-[3-[[[(Benzyloxyamino)carbonyl]-oxy]ethyl]-7-oxabicyclo[2.2.1]hept-2-yl]-5-heptenoic acid Following the procedure of Example 13 except substituting benzyloxyamine for butylamine, the title compound is obtained.

EXAMPLE 20

[1β,2α(5Z),3β,4β]-7-[3-[[[[(Ethyl)phenylamino]-carbonyl]oxy]ethyl]-7-oxabicyclo[2.2.1]hept-2-yl]-5-heptenoic acid Following the procedure of Example 14 except substituting (ethyl)phenylamine for butylamine, the title compound is obtained.

EXAMPLE 21

(1β,2β,3α,4β)-7-[3-[[[[(Cyclopentyl)methylamino]-carbonyl]oxy]ethyl]-7-oxabicyclo[2.2.1]hept-2-yl]-heptanoic acid Following the procedure of Example 15 except substituting (cyclopentyl)methylamine for butylamine, the title compound is obtained.

EXAMPLE 22

[1β,2α(5Z),3α,4β]-7-[3-[[[(Phenethylamino)-carbonyl]oxy]ethyl]-7-oxabicyclo[2.2.1]hept-2-yl]-5-heptenoic acid Following the procedure of Example 13 except substituting phenethylamine for butylamine, the title product is obtained.

EXAMPLE 23

[1β,2α(5Z),3α,4β]-7-[3-[[[(Butylamino)carbonyl]-oxy]-butyl]-7-oxabicyclo[2.2.1]hept-2-yl]-5-heptenoic acid A. [1β,2α(5Z),3α,4β]-7-[-(3-(3-Oxo)propyl-7-oxabicyclo[2.2.1]hept-2-yl]-5-heptenoic acid, methyl ester Following the procedure of Example 13, part A except substituting [1β,2α(5Z),3α,4β]-7-[3-(2-oxo)-ethyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title A compound is obtained.

B. [1β,2α(5Z),3α,4β]-7-[3-(4-Oxo)propyl-7-oxabicyclo[2.2.1]hept-2-yl]-5-heptenoic acid, methyl ester Following the procedure of Example 13, part A, except substituting the aldehyde from Part A above, for [1β,2α(5Z),3α,4β]-7-[3-formyl-7-oxabicylo[2.2.1]-hept-2-yl]-5-heptenoic acid, methyl ester, the title B aldehyde is obtained.

C. [1β,2α(5Z),3α,4β]-7-[3-(4-Hydroxybutyl)-7-oxabicyclo[2.2.1]hept-2-yl]-5-heptenoic acid, methyl ester Following the procedure of Example 13, part B, except substituting the title B aldehyde for [1β,2α(5Z)-,3α,4β]-7-[3-(2-oxo)ethyl-7-oxabicyclo[2.2.1]hept-2-yl]-

5-heptenoic acid, methyl ester, the title C alcohol is obtained.

D. [1β,2α(5Z),3α,4β]-7-[3-[[[(Butylamino)-carbonyl]oxy]butyl]-7-oxabicyclo[2.2.1]-hept-2-yl]-5-heptenoic acid Following the procedure of Example 1, except substituting the above part C alcohol for the alcohol used in Example 1, the title compound is obtained.

EXAMPLE 24

[1β,2α(5Z),3α,4β]-7-[3-[[[(Cyclohexylamino)carbonyl]-oxy]butyl]-7-oxabicyclo[2.2.1]hept-2-yl]-5-heptenoic acid Following the procedure of Example 23 except substituting cyclohexylamine for butylamine the title compound is obtained.

EXAMPLE 25

[1β,2α(5Z),3α,4β]-7-[3-[[[(Ethoxyamino)carbonyl]-oxy]butyl]-7-oxabicyclo[2.2.1]hept-2-yl]-5-heptenoic acid Following the procedure of Example 23 except substituting ethoxyamine for butylamine, the title compound is obtained.

EXAMPLE 26

(1β,2β,3α,4β)-7-[3-[[[(Benzylamino)carbonyl]oxy]-butyl]-7-oxabicyclo[2.2.1]hept-2-yl]heptanoic acid Following the procedure of Example 25 except substituting benzylamine for butylamine, the title compound is obtained.

EXAMPLE 27

[1β,2α(5Z),3α,4β]-7-[3-[[[(Benzyloxyamino)carbonyl]-oxy]butyl]-7-oxabicyclo[2.2.1]hept-2-yl]-5-heptenoic acid Following the procedure of Example 23 except substituting benzyloxyamine for butylamine, the title compound is obtained.

EXAMPLE 28

[1β,2α(5Z),3α,4β]-7-[3-[[[[(Ethyl)phenylamino]-carbonyl]oxy]butyl ]-7-oxabicyclo[2.2.1]hept-2-yl]-5-heptenoic acid Following the procedure of Example 23 except substituting (ethyl)phenylamine for butylamine, the title compound is obtained.

What is claimed is:
1. A compound having the structural formula

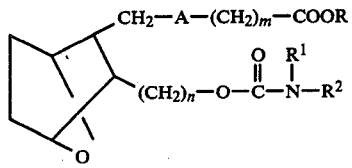

and including all stereoisomers thereof;
wherein A is CH=CH or (CH₂)₂;
m is 1 to 8; n is 1 to 5; R is H or lower alkyl; and R¹ and R² may be the same or different and are selected from the group consisting of hydrogen, lower alkyl, aryl, aralkyl, lower alkoxy, aralkoxy or cycloalkyl with the proviso that at least one of R¹ and R² is other than hydrogen, wherein the term "alkyl" used alone or as part of another group contains from 1 to 12 carbons and which may be unsubstituted or include a halo-substituent, an alkoxy substituent, an aryl substituent, an alkyl-aryl substituent, a haloaryl substituent, a cycloalkyl substituent or an alkylcycloalkyl substituent, the term "aryl" used alone or as part of another group refers to monocyclic or bicyclic aromatic groups containing 6 to 10 carbons in the ring portion and which may be unsubstituted or be substituted with lower alkyl, halogen or lower alkoxy, and the term "cycloalkyl" used alone or as part of another group includes saturated cyclic hydrocarbon groups containing 3 to 12 carbons and which may be unsubstituted or be substituted with 1 or 2 halogens, 1 or 2 lower alkyl groups and/or lower alkoxy groups.

2. The compound as defined in claim 1 having the formula

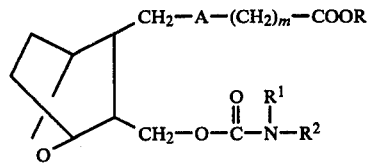

wherein R is hydrogen, R¹ is hydrogen and R² is lower alkyl, alkoxy or aralkoxy including all stereoisomers thereof.

3. The compound as defined in claim 1 wherein n is 1.

4. The compound as defined in claim 2 wherein A is CH=CH.

5. The compound as defined in claim 4 wherein R² is butyl, pentyl, hexyl or heptyl.

6. The compound as defined in claim 1 having the name [1β,2α(5Z),3α,4β]-7-[3-[[[(butylamino) carbonyl]oxy]methyl]-7-oxabicyclo[2.2.1]-hept-2-yl]-5-heptenoic acid or the methyl ester thereof or all stereoisomers thereof.

7. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

8. The method as defined in claim 7 wherein said compound is administered in an amount within the range of from about 1 to about 100 mg/kg.

9. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

10. A method of inhibiting platelet aggregation which comprises administering to a mammalian host an effective amount of a compound as defined in claim 1 or a pharmaceutically accetable salt thereof.

11. A method of inhibiting bronchoconstriction associated with asthma, which comprises administering to a mammalian host an effective amount of a compound as defined in claim 1 or a pharmaceutically acceptable salt thereof.

12. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,466,979
DATED : August 21, 1984
INVENTOR(S) : Jagabandhu Das et al.

It is certified that error appears in the above—identified patent and that said Letters Patent is hereby corrected as shown below:

Column 9, line 46, after "7-" and before "[[[(" insert
  -- [3- --.

Signed and Sealed this

Fifth Day of March 1985

[SEAL]

Attest:

DONALD J. QUIGG

Attesting Officer    Acting Commissioner of Patents and Trademarks